(12) United States Patent
Kim et al.

(10) Patent No.: US 12,337,075 B2
(45) Date of Patent: Jun. 24, 2025

(54) EXTRACELLULAR MATRIX-BASED BIOADHESIVE

(71) Applicants: POSTECH Research and Business Development Foundation, Pohang-si (KR); Konkuk University Industrial Cooperation Corp, Seoul (KR)

(72) Inventors: Hyeon Ji Kim, Changwon-si (KR); Je Hwan Jang, Seoul (KR); Won Il Han, Pohang-si (KR); Joon Young Kim, Seoul (KR); Jin Ah Jang, Pohang-si (KR); Dong Woo Cho, Seoul (KR)

(73) Assignees: POSTECH RESEARCH AND BUSINESS DEVELOPMENT FOUNDATION, Pohang-si (KR); KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 75 days.

(21) Appl. No.: 17/936,385

(22) Filed: Sep. 29, 2022

(65) Prior Publication Data

US 2023/0111780 A1 Apr. 13, 2023

(30) Foreign Application Priority Data

Oct. 8, 2021 (KR) .......................... 10-2021-0133757

(51) Int. Cl.
*A61L 24/00* (2006.01)
*A61L 24/10* (2006.01)

(52) U.S. Cl.
CPC .......... *A61L 24/0031* (2013.01); *A61L 24/104* (2013.01)

(58) Field of Classification Search
CPC ..................... A61L 24/0031; A61L 24/104
See application file for complete search history.

(56) References Cited

U.S. PATENT DOCUMENTS

2013/0280801 A1* 10/2013 Sun ................. A61L 27/222
 435/351
2018/0355127 A1* 12/2018 Lim ..................... C08K 5/56

FOREIGN PATENT DOCUMENTS

WO 20160140494 * 12/2016
WO 20180125776 * 11/2018

OTHER PUBLICATIONS

Saldin et al. Acta Biomaterialia 49 (2017) 1-15.*
Hyeonji Kim et al., "Light-Activated Decellularized Extracellular Matrix-Based Bioinks for Volumetric Tissue Analogs at the Centimeter Scale", Advanced Functional Materials, vol. 31, Issue 32, May 13, 2021. https://doi.org/10.1002/adfm.202011252.

* cited by examiner

*Primary Examiner* — Shirley V Gembeh
(74) *Attorney, Agent, or Firm* — LEX IP MEISTER, PLLC

(57) ABSTRACT

An embodiment of the present disclosure provides an extracellular matrix-based bioadhesive as an adhesive in the form of a composition including an extracellular matrix-containing hydrogel and a gelatin curing agent, wherein the extracellular matrix-containing hydrogel is gelatinized. Since the extracellular matrix-based bioadhesive according to an embodiment of the present disclosure has the same or similar rheological properties as gelatin, the bioadhesive has flowability at a temperature of 30° C. or higher and may be evenly and easily applied to a lesion site in the body. In addition, the extracellular matrix-based bioadhesive according to an embodiment of the present disclosure may adhere well to the lesion site because of a level of adhesive strength that is about 2 to 6 times higher than that of fibrin glue used as a commercial tissue adhesive. In addition, the extracellular matrix-based bioadhesive according to an embodiment of the present disclosure is based on a tissue-derived extracellular matrix, and thus includes a tissue-derived wound healing component or a tissue regeneration component, and may be used for wound healing or tissue regeneration in addition to bioadhesive applications.

4 Claims, 4 Drawing Sheets

[FIG. 1]
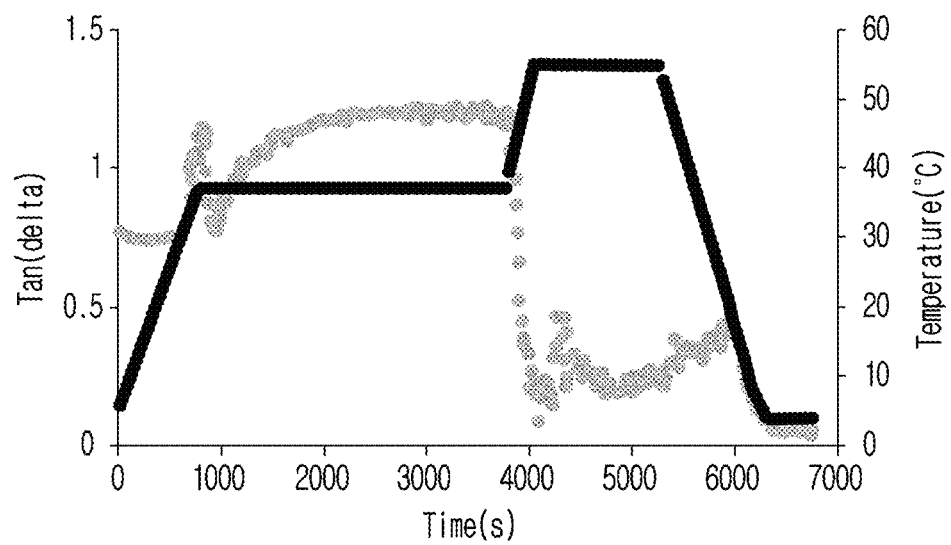

[FIG. 2]
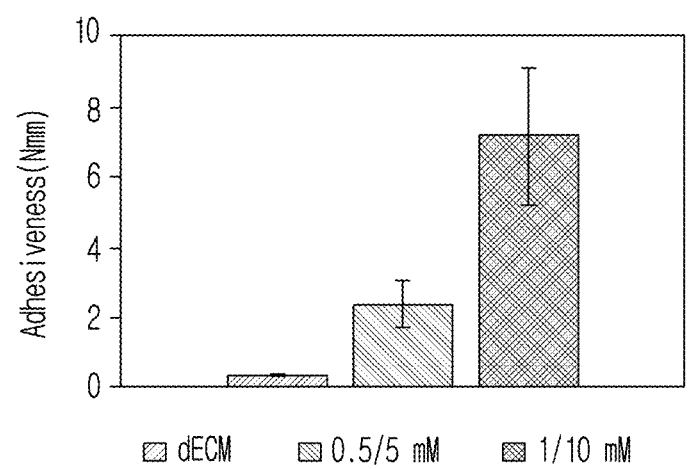

[FIG. 3]
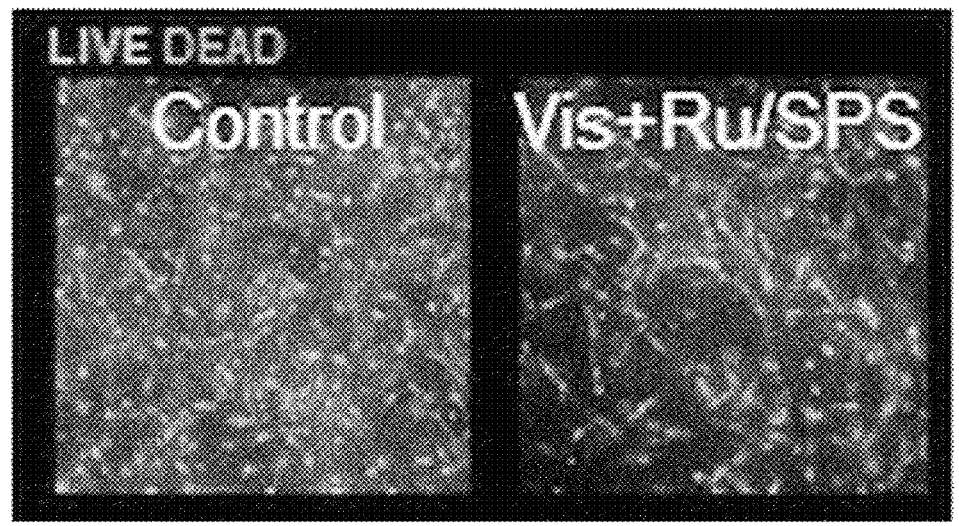

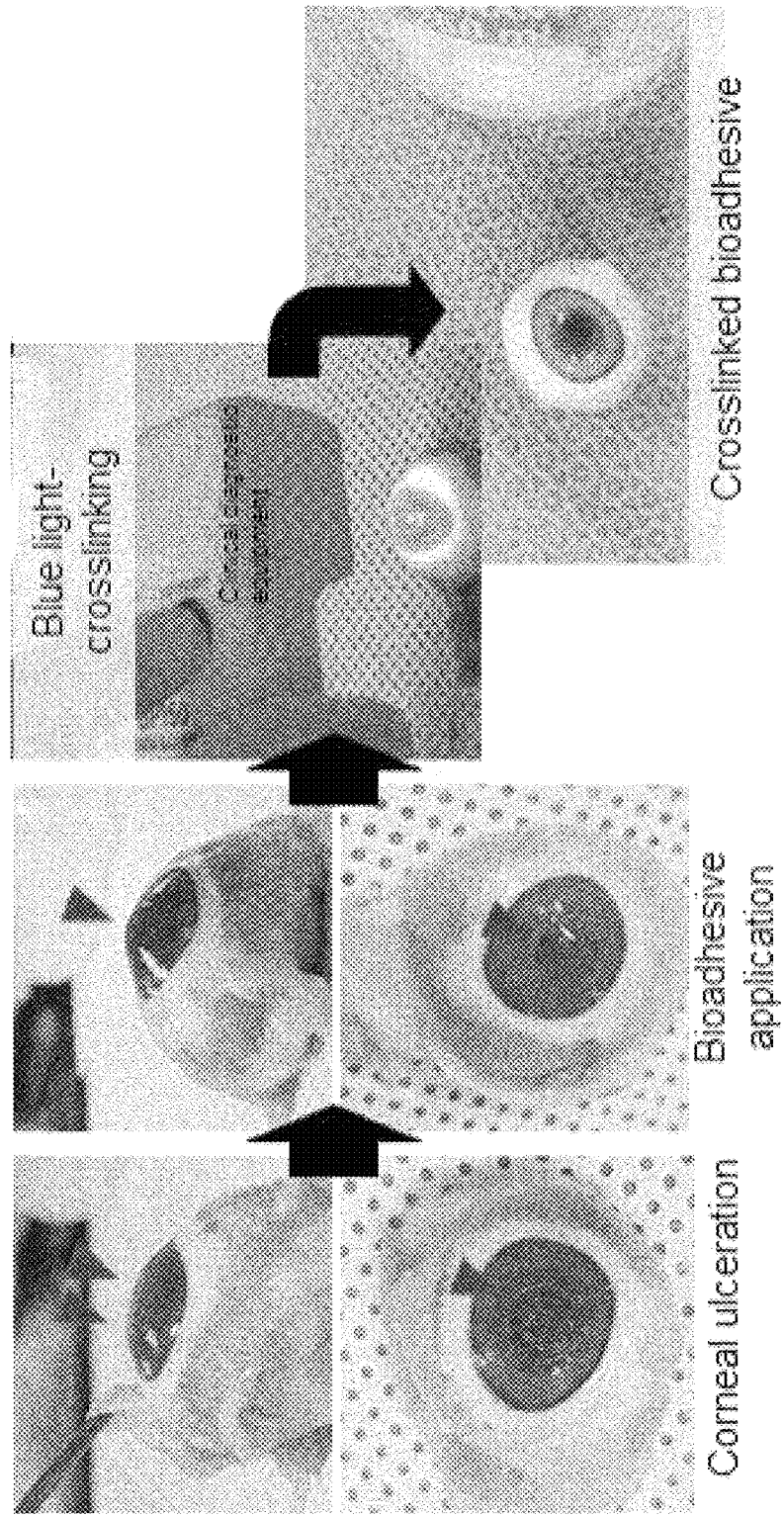
[FIG. 4]

EXTRACELLULAR MATRIX-BASED BIOADHESIVE

CROSS-REFERENCE TO RELATED APPLICATIONS

This application is based on and claims priority from Korean Patent Application No. 10-2021-0133757, filed on Oct. 8, 2021, with the Korean Intellectual Property Office, the disclosure of which is incorporated herein in its entirety by reference.

TECHNICAL FIELD

The present disclosure relates to a bioadhesive, and more particularly, to a bioadhesive based on an extracellular matrix and having excellent bioadhesive ability, a manufacturing method therefor, and a use thereof.

BACKGROUND

A bioadhesive is a generic term for adhesive materials used for bonding between living tissues such as skin, blood vessels, intestines, and bones, or for bonding between artificial materials and living tissues. Materials with adhesion properties are mainly used in various biological samples such as cells and proteins of living organisms. A bioadhesive may be applied in various clinical fields such as tissue adhesives, hemostatic agents, supporters for tissue engineering, hydrogels for drug delivery, tissue fillers, and wound healing. A bioadhesive requires strong adhesion and crosslinking ability, and needs to maintain its function in the living body for a long period of time. In addition, there should be no heat or harmful substances and no rejection reaction for instantaneous adhesion in the living body in the presence of tissue fluid.

Bioadhesives that are currently commercialized or put to practical use include cyanoacrylate instant adhesives, fibrin glues, gelatin glues, and polyurethane-based adhesives. However, a bioadhesive using a synthetic polymer shows very weak strength in the presence of an aqueous solution in the living body, and cyanoacrylate-based, gelatin-based, and polyurethane-based bioadhesives have been reported to be toxic in vivo, and have a major limitation in causing side effects such as immune responses to the human body. In addition, the fibrin-based bioadhesives currently used in actual patients have few side effects, but have a very low level of adhesion ability, so there is a limit to their use. In addition, most bioadhesives that are currently commercialized or put to practical use have an issue of hindering self-healing of a lesion site and inhibiting tissue regeneration due to low bioactivity. In order to address these issues, it is necessary to develop an ideal type of a bioadhesive that may have strong adhesion and crosslinking ability, show minimal side effects in vivo, and help tissue regeneration.

Upon reviewing the related art related to a bioadhesive, Korean Patent No. 10-1828434 discloses a bioadhesive composition including a novel compound having a gallic acid structure and a cyanoacrylate structure as an active ingredient. In addition, Korean Patent No. 10-1749791 discloses a composition for producing a bioadhesive for hard tissues containing modified cyanoacrylate and diacrylate. In addition, Korean Patent No. 10-1442479 discloses a biobinding agent including collagen, isinglass, and water in a weight ratio of 2:0.5 to 2.5:0.5 to 1.5. In addition, Korean Patent No. 10-1477708 discloses a biological glue including a cyanoacrylate component and an EGF microsphere component being composed of chitosan scattered among a PLCL matrix of a biodegradable polymer. In addition, Korean Patent No. 10-1472745 discloses a bioadhesive agent containing surface-modified hydroxyapatite.

SUMMARY

The present disclosure has been contrived under the conventional technological background, and an aspect of the present disclosure is to provide a bioadhesive based on an extracellular matrix and having excellent bioadhesive ability, and a manufacturing method therefor. In addition, an aspect of the present disclosure is to provide a use of the bioadhesive.

In the process of developing an extracellular matrix-based bioadhesive, the present inventors denatured a hydrogel containing an extracellular matrix into a hydrogel having gelatin properties through a predetermined heat treatment, and identified that when a gelatin curing agent was added thereto, it might be applied evenly in the body, exhibited excellent tissue bioadhesive ability, and might help tissue regeneration. Then, the present disclosure was completed.

An embodiment of the present disclosure provides an extracellular matrix-based bioadhesive as an adhesive in the form of a composition including an extracellular matrix-containing hydrogel and a gelatin curing agent, wherein the extracellular matrix-containing hydrogel is gelatinized.

As used herein, the term "extracellular matrix (ECM)" is an extracellular part of animal tissue that normally provides structural support to animal cells while performing a variety of other important functions. The extracellular matrix is a term to define connective tissue in animals and consists of various types of proteins including collagen, glycosaminoglycan (GAG), and the like. This extracellular matrix can be tissues of animals such as pigs and cattle and can be extracted from various organs.

As used herein, the term "gelatinized" refers to a state in which an extracellular matrix-containing hydrogel is denatured by heat and has the same or similar rheological properties as gelatin. Gelatin is a kind of induced protein obtained when collagen is treated with hot water, and only swells in cold water, but dissolves in hot water to form a sol and has flowability.

As used herein, the term "gelatin curing agent" refers to a substance or combination of substances that converts gelatin into a solid phase by crosslinking gelatin by simple addition, heat treatment, or light irradiation. Specific examples of the gelatin curing agent include a combination of ruthenium and sodium persulfate that induces curing of gelatin by irradiation with visible light (especially blue light); riboflavin that induces curing of gelatin by irradiation with ultraviolet light; or a combination of EDC/NHS [(1-ethyl-3-(3-dimethylaminopropyl)carbodiimide hydrochloride/N-hydroxysuccinimide]) that induces curing of gelatin by simple addition or a predetermined heat treatment, grape seed extract, dialdehyde starch, glutaraldehyde, and the like.

In the extracellular matrix-based bioadhesive according to an embodiment of the present disclosure, the extracellular matrix is preferably a decellularized extracellular matrix in consideration of a bio-application. The decellularized extracellular matrix has an effect of minimizing the immune response during allograft or xenograft by removing cells that may act as antigens inducing an immune response. Since the type and number of cells and the physical properties of the tissue itself are different depending on the tissue, decellularization is performed using various chemicals such as acids, bases, hypotonic solutions, hypertonic solutions, and detergents. In addition, the extracellular matrix is used while maintaining the structure of the tissue itself through only the decellularization process, but is used after freeze-drying and pulverizing process, then dissolved in an acidic solution or neutralized again to form a hydrogel. Further, the extracellular matrix preferably is a corneal-derived decellularized extracellular matrix in consideration of mainly applied uses. The corneal-derived decellularized extracellular matrix is derived from the corneal stromal tissue, and includes proteins that help cell adhesion in addition to the physical structure surrounding the cells or proteins that help cell growth and expression of functions. The corneal-derived decellularized extracellular matrix preferably includes collagen fibers from which telopeptide has been removed.

In the extracellular matrix-based bioadhesive according to an embodiment of the present disclosure, the extracellular matrix-containing hydrogel is preferably gelatinized by thermal denaturation of collagen, which is a component of the extracellular matrix. The collagen, as a major component of the extracellular matrix, is denatured and dissolved when heated with water, eluted in a colloidal phase, and converted into gelatin. Since collagen, which is a major component of the extracellular matrix, exists in a coagulated state at body temperature (about 37° C.) to which the bioadhesive is applied, it is difficult to apply the non-gelatinized extracellular matrix-containing hydrogel evenly and easily to a lesion site, and there is a discomfort in use. In addition, the non-gelatinized extracellular matrix-containing hydrogel does not easily harden even when a gelatin curing agent is added, and when applied to a lesion, the adhesive strength is greatly reduced.

In the extracellular matrix-based bioadhesive according to an embodiment of the present disclosure, the gelatin curing agent is preferably selected from a combination of ruthenium and sodium persulfate or riboflavin in consideration of biosafety, ease of use, and adhesive ability, and more preferably, the gelatin curing agent is selected from a combination of ruthenium and sodium persulfate. The ruthenium and sodium persulfate oxidize aromatic residues including tyrosine when irradiated with visible light (especially blue light), and the oxidized aromatic residues are converted into free radical forms and are covalently bonded to each other, for example, it is known to induce a crosslinking reaction by forming a di-tyrosine covalent bond. In addition, when the gelatin curing agent is selected from a combination of ruthenium and sodium persulfate, it is preferable that the concentration of ruthenium in the bioadhesive is 0.1 to 2 mM and the concentration of sodium persulfate is 1 to 20 mM in consideration of biosafety and adhesive ability. More preferably, the concentration of ruthenium is 0.2 to 1.5 mM and the concentration of sodium persulfate is 2 to 15 mM.

An embodiment of the present disclosure provides a method for manufacturing an extracellular matrix-based bioadhesive, wherein the method includes: preparing an extracellular matrix-containing hydrogel neutralized by adjusting a pH of the extracellular matrix-containing hydrogel to 6 to 8.5; heat-treating the neutralized extracellular matrix-containing hydrogel at a temperature of 50 to 60° C. to denature collagen, which is a component of an extracellular matrix, to obtain a gelatinized extracellular matrix-containing hydrogel; and adding and mixing a gelatin curing agent to the gelatinized extracellular matrix-containing hydrogel to obtain a bioadhesive.

In the method for manufacturing the extracellular matrix-based bioadhesive according to an embodiment of the present disclosure, the extracellular matrix is preferably a decellularized extracellular matrix, and more preferably a corneal-derived decellularized extracellular matrix.

In addition, in the method for manufacturing the extracellular matrix-based bioadhesive according to an embodiment of the present disclosure, the extracellular matrix content in the extracellular matrix-containing hydrogel is not significantly limited. In consideration of hydrogel forming ability, smooth thermal denaturation, uniform mixing with a gelatin curing agent, or ease of use or adhesive strength of the bioadhesive, it is preferably 1% to 4% (w/v), and more preferably 1.5% to 3% (w/v).

In addition, in the method for manufacturing the extracellular matrix-based bioadhesive according to an embodiment of the present disclosure, the heat treatment temperature for gelatinization of the neutralized extracellular matrix-containing hydrogel is preferably 52 to 58° C. in consideration of smooth thermal denaturation. In addition, the heat treatment time of the neutralized extracellular matrix-containing hydrogel is preferably 10 to 40 minutes in consideration of smooth thermal denaturation, and more preferably 15 to 30 minutes.

In addition, in the method for manufacturing the extracellular matrix-based bioadhesive according to an embodiment of the present disclosure, the gelatin curing agent is preferably added when the temperature of the gelatinized extracellular matrix-containing hydrogel is 30° C. to 45° C. for uniform mixture, and more preferably 32 to 40° C. The gelatin curing agent is preferably selected from a combination of ruthenium and sodium persulfate or riboflavin, and more preferably from a combination of ruthenium and sodium persulfate, in consideration of biosafety, ease of use, and adhesive ability. In addition, when the gelatin curing agent is selected from a combination of ruthenium and sodium persulfate, in consideration of biosafety and adhesive ability, it is preferable that the concentration of ruthenium in the bioadhesive is added to be 0.1 to 2 mM and the concentration of sodium persulfate is added to be 1 to 20 mM. It is more preferable that the concentration of ruthenium is added to be 0.2 to 1.5 mM, and the concentration of sodium persulfate is added to be 2 to 15 mM.

The method for manufacturing the extracellular matrix-based bioadhesive according to an embodiment of the present disclosure includes applying the bioadhesive to a lesion site and applying heat or irradiating light. For example, when the extracellular matrix-based bioadhesive includes a combination of ruthenium and sodium persulfate as a gelatin curing agent, by applying the bioadhesive to the lesion site and irradiating visible light, particularly blue light with a wavelength of 400 to 450 nm, a bioadhesive film with excellent adhesive strength may be formed.

An embodiment of the present disclosure provides a composition for wound healing or tissue regeneration including the aforementioned extracellular matrix-based bioadhesive. In addition, an embodiment of the present disclosure provides a composition for wound healing or tissue regeneration including the bioadhesive manufactured by the aforementioned method. The extracellular matrix-based bioadhesive according to an embodiment of the present disclosure includes, in addition to the gelatinized collagen component, a transforming growth factor-beta-induced protein, which is a major component of wound healing; decorin, which is a major component of tissue regeneration; and keratocan and aldehyde dehydrogenase that control tissue function, the bioadhesive may be used for wound healing or tissue regeneration in addition to bioadhesive applications.

Since the extracellular matrix-based bioadhesive according to an embodiment of the present disclosure has the same or similar rheological properties as gelatin, the bioadhesive has flowability at a temperature of 30° C. or higher and may be evenly and easily applied to a lesion site in the body. In addition, the extracellular matrix-based bioadhesive according to an embodiment of the present disclosure may adhere well to the lesion site because of a level of adhesive strength that is about 2 to 6 times higher than that of fibrin glue used as a commercial tissue adhesive. In addition, the extracellular matrix-based bioadhesive according to an embodiment of the present disclosure is based on a tissue-derived extracellular matrix, and thus includes a tissue-derived wound healing component or a tissue regeneration component, and may be used for wound healing or tissue regeneration in addition to bioadhesive applications.

BRIEF DESCRIPTION OF THE DRAWINGS

FIG. 1 is a graph showing the results of time sweep analysis of the neutralized corneal-derived decellularized extracellular matrix (Co-dECM) hydrogels prepared in an example embodiment of the present disclosure (black line: temperature profile; gray line: loss tangent [Tan(delta)]).

FIG. 2 is a graph showing the results of analyzing the adhesive ability of the extracellular matrix-based bioadhesive prepared in an example embodiment of the present disclosure. In FIG. 2, the term "dECM" refers to a neutralized Co-dECM hydrogel, the term "0.5/5 mM" refers to the extracellular matrix-based bioadhesive prepared in Preparation Example 1, and the term "1/10 mM" refers to the extracellular matrix-based bioadhesive prepared in Preparation Example 2.

FIG. 3 is an image of measuring the cytotoxicity of the extracellular matrix-based bioadhesive prepared in an example embodiment of the present disclosure. In FIG. 3, the term "Control" on the left refers to a neutralized Co-dECM hydrogel, and the term "Vis+Ru/SPS" on the right refers to the extracellular matrix-based bioadhesive prepared in Preparation Example 2.

FIG. 4 is an image showing the process and results of applying the extracellular matrix-based bioadhesive prepared in Preparation Example 1 in vitro of example embodiments of the present disclosure.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in more detail through example embodiments. However, the following example embodiments are only for clearly illustrating the technical features of the present disclosure, and do not limit the scope of right of the present disclosure.

1. Preparation of Corneal-Derived Decellularized Extracellular Matrix (Co-dECM) and Hydrogel Containing the Same Corneal-derived decellularized extracellular matrix (Co-dECM) was prepared as follows (See. Kim H, Park M N, Kim J, Jang J, Kim H K and Cho D W 2019 Characterization of cornea-specific bioink: high transparency, improved in vivo safety J. Tissue Eng. 10). First, the entire cornea incised from the pig's eye was washed with a PBS buffer solution containing 100 units/ml of penicillin and 0.1 mg/ml of streptomycin. Thereafter, the epithelium and endothelium were removed from the corneal tissue to obtain a pure corneal stromal layer. Thereafter, the matrix tissue was placed in a 20 mM ammonium hydroxide solution ($NH_4OH$; 4.98 N aqueous solution) containing 0.5% Triton X-100, and the mixture was stirred for about 4 hours. Thereafter, the matrix tissue was washed with distilled water and treated with a hypotonic Tris hydrochloride (Tris-HCl; pH 7.4) buffer solution for about 24 hours. Thereafter, the matrix tissue was placed in a 10 mM Tris-HCl solution containing 1% (v/v) Triton X-100, and the mixture was stirred at 37° C. for about 24 hours to obtain a corneal-derived decellularized extracellular matrix (Co-dECM) tissue. Thereafter, the corneal decellularized extracellular matrix (Co-dECM) tissue was sterilized by treatment with 1% peracetic acid solution in 50% ethanol for about 10 hours. After completion of the decellularization process, corneal-derived decellularized extracellular matrix (Co-dECM) was freeze-dried overnight and ground into a fine powder using liquid nitrogen and a grinding device. 0.2 g Co-dECM powder was added to 10 ml of acetic acid solution (0.5 M) supplemented with 0.02 g pepsin, and the mixture was uniformly stirred through vortexing, and treated for about 3 days to remove telopeptides in collagen molecules and be completely dissolved to obtain a corneal-derived decellularized extracellular matrix hydrogel having a pH of about 3 to 4 and a corneal-derived decellularized extracellular matrix (Co-dECM) concentration of 2% (w/v). The 2% (w/v) Co-dECM hydrogel was filtered through a 10 μm mesh and stored at 4° C., and used for subsequent experiments.

2. Preparation of Extracellular Matrix-Based Bioadhesive

Preparation Example 1

A 10 N concentration of sodium hydroxide solution was added to the 2% (w/v) Co-dECM hydrogel and stirred to be neutralized to a pH of 7.0 to 7.4. Thereafter, the neutralized Co-dECM hydrogel was heated to 55° C., maintained for 20 minutes, and thermal denaturalized, thereby obtaining the gelatinized Co-dECM hydrogel. Then, when the gelatinized Co-dECM hydrogel was cooled slowly at room temperature to about 37° C., photocuring agents ruthenium and sodium persulfate were added so that the final concentrations became 0.5 mM and 5 mM, respectively, and stirred to prepare a bioadhesive. All solvents of the ruthenium solution and the sodium persulfate solution were Dulbecco's phosphate-buffered saline (DPBS). When the bioadhesive is irradiated with a visible light having a wavelength of about 400 to 450 nm, the tyrosine residues present in the gelatinized Co-dECM hydrogel are oxidized and converted into tyrosine free radicals, and curing is promoted by forming a di-tyrosine covalent bond with a nearby tyrosine residue.

Preparation Example 2

A 10 N concentration of sodium hydroxide solution was added to the 2% (w/v) Co-dECM hydrogel and stirred to be neutralized to a pH of 7.0 to 7.4. Thereafter, the neutralized Co-dECM hydrogel was heated to 55° C., maintained for 20 minutes, and thermal denaturalized, thereby obtaining the gelatinized Co-dECM hydrogel. Then, when the gelatinized Co-dECM hydrogel was cooled slowly at room temperature to about 37° C., photocuring agents ruthenium and sodium persulfate were added so that the final concentrations became 1 mM and 10 mM, respectively, and stirred to prepare a bioadhesive. All solvents of the ruthenium solution and the sodium persulfate solution were Dulbecco's phosphate-buffered saline (DPBS).

3. Observation of Phase Change of Co-dECM Hydrogel during Thermal Denaturation Process A 10 N concentration of sodium hydroxide solution was added to the 2% (w/v) Co-dECM hydrogel and stirred to be neutralized to a pH of 7.0 to 7.4. Thereafter, the phase change according to the heat treatment of the neutralized Co-dECM hydrogel was measured using an advanced hybrid rheometer equipped with a 25 mm diameter plate. Specifically, the time sweep analysis was performed while applying a predetermined temperature profile over time to the neutralized Co-dECM hydrogel, and Tan (delta) at 10% strain was measured. FIG. 1 is a graph showing the results of time sweep analysis of the neutralized corneal-derived decellularized extracellular matrix (Co-dECM) hydrogels prepared in an example embodiment of the present disclosure (black line: temperature profile; gray line: loss tangent [Tan (delta)]). As shown in FIG. 1, when the neutralized Co-dECM hydrogel was heated to a preset temperature profile, a total of three phase changes occurred. Specifically, when the neutralized Co-dECM hydrogel was heated from 4° C. to 37° C., a primary phase change occurred at 37° C. The primary phase change means that the Co-dECM hydrogel, of which major component is collagen, is cured. Thereafter, the temperature condition was maintained at 37° C. for about 3,000 seconds to stabilize the gelation deformation, and then, the Co-dECM hydrogel was heated to 55° C., at which time a secondary phase change occurred. The secondary phase change means that collagen, which is a major component of the Co-dECM hydrogel, is gelatinized through thermal denaturation after curing. Thereafter, the temperature condition was maintained at 55° C. for about 1,200 seconds to stabilize the thermal denaturation process, and then the Co-dECM hydrogel was cooled to 4° C., at which time a tertiary phase change occurred. The tertiary phase change means that the gelatinized Co-dECM hydrogel is solidified according to temperature in accordance with the properties of gelatin.

4. Component Analysis of Gelatinized Corneal-Derived Decellularized Extracellular Matrix (Co-dECM) Hydrogel A 10 N concentration of sodium hydroxide solution was added to the 2% (w/v) Co-dECM hydrogel and stirred to be neutralized to a pH of 7.0 to 7.4. Thereafter, the neutralized Co-dECM hydrogel was heated to 55° C., maintained for 20 minutes, and thermal denaturalized, thereby obtaining the gelatinized Co-dECM hydrogel. Thereafter, the gelatinized Co-dECM hydrogel was freeze-dried and then pulverized to make powder, and the components were analyzed using a proteomics analysis method. In Table 1 below, 15 major components, which are the results of proteomics analysis of the gelatinized Co-dECM hydrogel, are summarized.

TABLE 1

| Matrisome | Description of Components | Component content (weight %) |
| --- | --- | --- |
| Collagens | collagen alpha-1 (I) chain isoform X1 [Sus scrofa] | 44.34 |
| Collagens | collagen alpha-2 (I) chain precursor [Sus scrofa] | 26.71 |
| Collagens | collagen alpha-1 (II) chain [Sus scrofa] | 8.94 |
| Collagens | collagen alpha-3 (VI) chain [Sus scrofa] | 6.70 |
| Collagens | collagen alpha-1 (XII) chain isoform X1 [Sus scrofa] | 0.66 |
| Collagens | collagen alpha-2 (VI) chain [Sus scrofa] | 0.61 |
| Collagens | collagen alpha-2 (V) chain precursor [Sus scrofa] | 0.56 |
| ECM Glycoproteins | thrombospondin type-1 domain-containing protein 4 isoform X1 [Sus scrofa] | 0.22 |
| ECM Regulators | pigment epithelium-derived factor isoform X1 [Sus scrofa] | 0.20 |
| Proteoglycans | decorin precursor [Sus scrofa] | 0.20 |
| Proteoglycans | keratocan [Sus scrofa] | 0.18 |
| Proteoglycans | aldehyde dehydrogenase, dimeric NADP-preferring [Sus scrofa] | 0.17 |
| Collagens | collagen alpha-1 (V) chain precursor [Sus scrofa] | 0.16 |
| Collagens | collagen alpha-1 (XI) chain [Sus scrofa] | 0.07 |
| ECM Glycoproteins | transforming growth factor-beta-induced protein ig-h3 [Sus scrofa] | 0.06 |

As shown in Table 1 above, the gelatinized Co-dECM hydrogel was identified to contain the most collagen component, and in addition, transforming growth factor-beta-induced protein, which is a major component of corneal wound healing; decorin, a major component of transparent corneal regeneration; and keratocan, aldehyde dehydrogenase, etc., which actually control corneal function, were identified to be contained.

5. Analysis of Adhesive Ability of Extracellular Matrix-Based Bioadhesive

After heating the extracellular matrix-based bioadhesives prepared in Preparation Examples 1 and 2 to about 30° C. to have flowability, 10 ml thereof per test was applied to a measurement reservoir provided in a texture analyzer and irradiated with blue light at an intensity of 10 mW/cm$^2$ for about 10 minutes to cure the bioadhesives. Then, the adhesive ability of the cured bioadhesives was measured. In addition, as a control group, the adhesive ability was measured after applying and curing the Co-dECM hydrogel neutralized to a pH of 7.0 to 7.4 in the same manner without the addition of a curing agent and without undergoing a thermal denaturation process. FIG. 2 is a graph showing the results of analyzing the adhesive ability of the extracellular matrix-based bioadhesive prepared in an example embodiment of the present disclosure. In FIG. 2, the term "dECM" refers to a neutralized Co-dECM hydrogel, the term "0.5/5 mM" refers to the extracellular matrix-based bioadhesive prepared in Preparation Example 1, and the term "1/10 mM" refers to the extracellular matrix-based bioadhesive prepared in Preparation Example 2. As shown in FIG. 2, as the content of the photocuring agent in the bioadhesive increased, the adhesive ability of the bioadhesive was improved. The adhesive ability of the extracellular matrix-based bioadhesives prepared in Preparation Examples 1 and 2 is 2 to 6 times higher than the adhesive strength of about 1.2 N·mm of fibrin glue used as a commercial tissue adhesive.

6. Cytotoxicity Evaluation of Extracellular Matrix-Based Bioadhesives

Differentiated keratocytes were prepared as follows (See. Park M N, Kim B, Kim H, Park S H, Lim M H, Choi Y J, Yi H G, Jang J, Kim S W and Cho D W 2017 Human turbinate-derived mesenchymal stem cells differentiated into keratocyte progenitor cells J. Clin. Exp. Ophthalmol. 8 627). Human turbinate derived mesenchymal stem cells (hTMSCs; obtained from Catholic University of Korea, St. Mary's Hospital) were placed in normal Dulbecco's Modified Eagle's Medium (DMEM) containing 10% (v/v) fetal bovine serum and 1% (v/v) penicillin/cultured in a humidified 5% carbon dioxide atmosphere and a temperature of 37° C. Then, in the second passage, the normal medium was replaced with a differentiation medium containing 10 ng/ml KGF/EGF and cultured for one day to obtain differentiated keratocytes. Thereafter, after applying the differentiated keratocytes obtained on the extracellular matrix-based bioadhesive prepared in Preparation Example 2, the cells were cultured for 4 days and the cell viability was observed to evaluate the cytotoxicity of the extracellular matrix-based bioadhesive. In addition, as a control group, the cell viability was observed after merely applying and culturing the cells in the same manner on the Co-dECM hydrogel neutralized to a pH of 7.0 to 7.4 without the addition of a curing agent and without undergoing a thermal denaturation process. FIG. 3 is an image of measuring the cytotoxicity of the extracellular matrix-based bioadhesive prepared in an example embodiment of the present disclosure. In FIG. 3, the term "Control" on the left refers to a neutralized Co-dECM hydrogel, and the term "Vis+Ru/SPS" on the right refers to the extracellular matrix-based bioadhesive prepared in Preparation Example 2. As shown in FIG. 3, both the neutralized Co-dECM hydrogel and the extracellular matrix-based bioadhesive prepared in Preparation Example 2 showed a cell viability of 95% or more, which was verified to have little cytotoxicity.

7. In Vitro Application of Extracellular Matrix-Based Bioadhesive

A 350 μm deep defect was made in the pig's eyes, and the extracellular matrix-based bioadhesive prepared in Preparation Example 1 was applied to the defected area. Thereafter, the bioadhesive was cured by irradiating blue light with a wavelength of 400 to 450 nm to the applied bioadhesive for about 3 minutes using a diagnostic device actually used for the evaluation of macular degeneration in ophthalmology. FIG. 4 is an image showing the process and results of applying the extracellular matrix-based bioadhesive prepared in Preparation Example 1 in vitro of example embodiments of the present disclosure. After curing the bioadhesive, it was identified that the bioadhesive did not fall off and adhered well to the corneal tissue of the pig even when pressure was applied to the pig's eyes by hand or a force was applied to a specific area with tweezers.

As described above, the present disclosure has been described through the above example embodiments, but the present disclosure is not necessarily limited thereto, and various modifications may be made without departing from the scope and spirit of the present disclosure. Accordingly the scope of protection of the present disclosure should be construed to include all embodiments falling within the scope of the claims appended to the present disclosure.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An extracellular matrix-based bioadhesive as an adhesive in the form of a composition including a gelatinized extracellular matrix-containing hydrogel and a gelatin curing agent,
    wherein the gelatinized extracellular matrix-containing hydrogel is obtained by heat-treating an extracellular matrix-containing hydrogel at a temperature of 50 to 60° C. and a pH of 6 to 8.5,
    wherein the extracellular matrix is a decellularized extracellular matrix,
    wherein the gelatinized extracellular matrix-containing hydrogel is obtained by thermal denaturation of collagen, which is a component of an extracellular matrix.

2. The extracellular matrix-based bioadhesive of claim 1, wherein the decellularized extracellular matrix is a corneal-derived decellularized extracellular matrix.

3. The extracellular matrix-based bioadhesive of claim 1, wherein the gelatin curing agent is selected from a combination of ruthenium and sodium persulfate or riboflavin.

4. The extracellular matrix-based bioadhesive of claim 3, wherein:
    the gelatin curing agent is a combination of ruthenium and sodium persulfate;
    a concentration of ruthenium in the bioadhesive is 0.1 to 2 mM; and
    a concentration of sodium persulfate is 1 to 20 mM.

* * * * *